United States Patent [19]

Ohmori et al.

[11] Patent Number: 5,232,913

[45] Date of Patent: Aug. 3, 1993

[54] ANTIHEPATOPATHIC COMPOSITION

[75] Inventors: Shinji Ohmori, Okayama; Kazumi Ogata, Toyonaka; Takahiro Sakaue, Itami, all of Japan

[73] Assignee: Senju Pharmaceutical Co., Ltd., Osaka, Japan

[21] Appl. No.: 778,134

[22] PCT Filed: Apr. 25, 1991

[86] PCT No.: PCT/JP91/00569

§ 371 Date: Dec. 13, 1991

§ 102(e) Date: Dec. 13, 1991

[87] PCT Pub. No.: WO91/16065

PCT Pub. Date: Oct. 31, 1991

[30] Foreign Application Priority Data

Apr. 26, 1990 [JP] Japan .................. 2-112260

[51] Int. Cl.$^5$ .............................................. C07K 5/06
[52] U.S. Cl. ......................................... 514/18; 514/19; 530/331
[58] Field of Search ................ 530/331; 514/18, 19, 514/534

[56] References Cited

U.S. PATENT DOCUMENTS

| | | | |
|---|---|---|---|
| 4,879,370 | 11/1989 | Meister | 530/331 |
| 4,927,808 | 5/1990 | Kitahara et al. | 530/331 |
| 5,081,149 | 1/1992 | Ohmori et al. | 514/534 |
| 5,093,478 | 3/1992 | Griffith et al. | 530/331 |
| 5,102,871 | 4/1992 | Furukawa et al. | 514/18 |

FOREIGN PATENT DOCUMENTS

| | | |
|---|---|---|
| 63-8337 | 1/1988 | Japan . |
| 2-255624 | 10/1990 | Japan . |
| 3-48626 | 3/1991 | Japan . |
| 3-112933 | 5/1991 | Japan . |
| 3-118334 | 5/1991 | Japan . |
| WO91/12262 | 8/1991 | PCT Int'l Appl. . |

OTHER PUBLICATIONS

Virtanen et al., Hoppe-Seyler's Z. Physiol. Chem., Bd. 322, pp. 8-20, 1960.
Suzuki et al., Chem. Pharm. Bull., vol. 9, pp. 77-78.

*Primary Examiner*—Lester L. Lee
*Attorney, Agent, or Firm*—Wenderoth, Lind & Ponack

[57] ABSTRACT

An antihepatopathic composition comprising a glutathione-S-lower fatty acid derivative of the formula

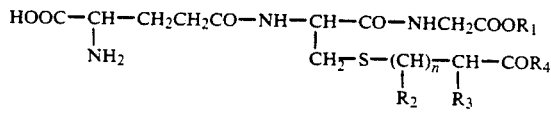

wherein $R_1$ and $R_3$ are the same or different and respectively mean a hydrogen atom or a lower alkyl group which may be substituted; $R_4$ is a hydroxyl group, a lower alkoxy group which may be substituted or an amino group which may be substituted; n means 0 or 1 and when $n=1$, $R_2$ is a hydrogen atom, a lower alkyl group which may be substituted or a phenyl group which may be substituted or a salt thereof as an active ingredient.

13 Claims, No Drawings

ANTIHEPATOPATHIC COMPOSITION

TECHNICAL FIELD

The present invention relates to an antihepatopathic composition containing a novel and useful glutathione-S-lower fatty acid derivative.

BACKGROUND ART

There are known several glutathione-S-lower fatty acid derivatives. Among them, S-(2-carboxypropyl)-glutathione has been isolated from onion and garlic (Virtanen and Matikkala, Hoppe-Seylers Z. Physiol. Chem., Bd 322, pages 8–20, 1960; Suzuki et al., Chem. Pharm. Bull., Vol. 9, pages 77–78, 1961) but there is little information on its pharmacologic activity.

The inventors of the present invention previously found that glutathione-S-succinic acid derivatives have platelet aggregation-inhibitory, antiinflammatory, antiallergic, antitumoral and hepatic impairment-protective activities (Japanese Kokai Patent Application No. 63-8337 and Japanese Patent Application No. 1-79956, No. 1-183484, No. 1-256370 and No. 2-36745).

In search of still more pharmacologically active compounds, the inventors of the present invention synthesized a variety of novel glutathione derivatives and screened them, as well as said S-(2-carboxypropyl)-glutathione, for their pharmacologic activities. As a consequence, they found that S-(2-carboxypropyl)-glutathione and a series of compounds which can be synthesized by reacting glutathione or an ester thereof with an $\alpha,\beta$-unsaturated fatty acid, such as acrylic acid, methacrylic acid, crotonic acid, cinnamic acid, etc., or an $\alpha$ (or $\beta$)-halogenated organic monocarboxylic acid, such as monochloroacetic acid, or an ester or amide thereof have excellent antihepatopathic efficacy. The present invention has been attained based on this finding.

DISCLOSURE OF THE INVENTION

The present invention relates to an antihepatopathic composition comprising a compound of the formula

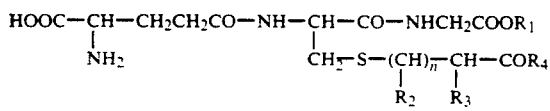

wherein $R_1$ and $R_3$ are the same or different and respectively mean a hydrogen atom or a lower alkyl group which may be substituted; $R_4$ is a hydroxyl group, a lower alkoxy group which may be substituted or an amino group which may be substituted; n means 0 or 1 and when $n=1$, $R_2$ is a hydrogen atom, a lower alkyl group which may be substituted or a phenyl group which may be substituted or a salt thereof as an active ingredient.

Where $R_1$, $R_3$ in the above formula means a lower alkyl group, such alkyl group preferably has 1 to 10 carbon atoms. This alkyl group may be straight-chain, branched or cyclic or contain a cyclic moiety. Thus, methyl, ethyl, n-propyl, isopropyl, cyclopropyl, n-butyl, tert-butyl, sec-butyl, n-pentyl, 1-ethylpropyl, isopentyl and benzyl may be mentioned by way of example.

Referring, further, to the above formula, where n is equal to 1, $R_2$ is a hydrogen atom, a lower alkyl group or a pheyl group. The lower alkyl group is as previously defined, and the phenyl group may be substituted with an alkyl group and so on.

Further in the formula, $R_4$ is a hydroxyl group, a lower alkoxy group or an amino group. The lower alkoxy group includes, among others, methoxy, ethoxy, propoxy, isopropoxy, n-pentyloxy, isopentyloxy, tert-pentyloxy, n-pentyloxy, isopentyloxy, tert-pentyloxy, neopentyloxy, 2-methylbutoxy, 1,2-dimethylpropoxy, 1-ethylpropoxy and so on. The lower alkoxy group may have a hydroxyl group or a cyclic group such as pehnyl. The hydrogen atom or atoms of said amino group may be substituted by, for example, alkyl.

In the antihepatopathic composition of the invention, the above compound can occur as the free acid or as a pharmaceutically acceptable salt thereof, for instance an alkali metal salt thereof, e.g. the sodium salt, potassium salt, etc., or an alkaline earth metal salt, e.g. the calcium salt, magnesium salt and so on. Regarding the salt, any or all of the carboxyl functions available in the compound may have been converted to such salt or salts. Any of these salts can be used advantageously in the manufacture of the antihepatopathic composition of the present invention.

This antihepatopathic composition effectively inhibits the onset of acute and chronic hepatic disorders, suppresses elevational of GOT and GPT values and, as such, is not only useful for the prevention and treatment of acute or chronic hepatitis but also effective in the prevention and treatment of hepatocirrhosis. It can also be used with advantage in cases of hepatic impairment induced by drugs such as acetaminophen.

The antihepatophathic composition of the present invention can be administered orally or parenterally. With regard to dosage form, it can be provided, for example, in various solid dosage forms such as tablets, granules, powders, capsules, etc. or in liquid dosage forms such as injectable preparations. These preparations can be manufactured by the established pharmaceutical procedures and according to the type or disease to be controlled. In such preparations, there may be incorporated conventional additives such as the binder, disintergrating agent, thickener, dispersing agent, reabsorption promoter, corrigent, buffer, surfactant, cosolvent, preservative, emulsifier, isotonizing agent, stabilizer, pH adjusting agent and so on.

The dosage of the active ingredient according to the present invention is dependent on the particular species of compound used, type of disease, patient's age and body weight, dosage form, indication and so on. In the case of an injectable preparation, for instance, about 1 to 500 mg per day per adult is administered once a day, and in the case of an oral preparation, about 10 to 2000 mg per dose per adult is administered a few times a day.

Depending on the objective and necessity of treatment, the antihepatopathic composition of the present invention may contain two or more species of the active compounds in suitable proportions.

Unless contrary to the object of the invention, the antihepatopathic composition of the present invention may additionally contain other active ingredients having similar efficacy or different efficacies in suitable proportions.

Among the compounds which can be used in the antihepatopathic composition of the invention, the compound wherein $n=1$, $R_1$ and $R_2$ are hydrogen, $R_3$ is methyl and $R_4$ is hydroxy is a known compound as mentioned hereinbefore and can be extracted from onion or garlic or chemically synthesized by, or in accordance with, the method described in Journal of Agricultural and Food Chemistry 37, 611 (1989). The compound described in Synthesis Example 1 which appears hereinafter is also a known compound. Thus, either glutathione or a glutathione monoester (γ-glutamylcysteinylglycine ester) which is obtainable by reacting glutathione with the corresponding alcohol in the presence of an acid, e.g. sulfuric acid, is reacted in water or aqueous medium with an α, β-unsaturated acid, e.g. acrylic acid, methacrylic acid, crotonic acid, cinnamic acid, etc., or an α (or β)-halogenated organic monocarboxylic acid, e.g. monochloroacetic acid, or an ester or amide thereof, preferably at pH about 4 to 8, at room temperature or under mild heating with stirring. This reaction readily goes to completion. This reaction mixture is purified by column chromatography or recrystallization from a solvent to give the object compound. Almost all of the compounds wherein $R_1$ is hydrogen can be purified by way of the copper salt.

Since most of the compounds synthesized as above have asymmetric carbon within the molecule, they may occur as optical isomers but all such optically active compounds as well as mixtures thereof can be used for purposes of the present invention.

The following synthesis examples, test example and preparation examples are intended to illustrate the invention in further detail.

SYNTHESIS EXAMPLE 1

S-(2-Carboxyethyl)glutathione

[$R_1 = R_2 = R_3 = H$, $R_4 = OH$, $n = 1$]

In 100 ml of water are dissolved 6.2 g of glutathione and 4 ml of acrylic acid and the solution is adjusted to pH 6.5 with sodium hydroxide and stirred at room temperature for 12 hours. Then, 5 ml of acetic acid and 4.4 g of copper acetate are added and dissolved, following by addition of 150 ml of ethanol. The precipitated copper salt is recovered by filtration and washed with 50% ethanol. From this salt, copper is removed using hydrogen slufide as described in Synthesis Example 2 and the filtrate is concentrated. To the residue is added ethanol and the resulting white crystalline precipitate is recovered by filtration and recrystallized from water-ethanol. Yield 5.4 g. TLC, silica gel Rf=0.15 (n-butanol-acetic acid-water=4:1:1)

Elemental analysis, for $C_{13}C_{21}O_8N_3S$: Calcd. (%): C, 41.16; H, 5.58; N, 11.08. Found (%): C, 40.97; H, 5.46; N, 11.12.

SYNTHESIS EXAMPLE 2

S-(2-Methyl-2-carbethoxypropyl)glutathione]

[=$R_2 = H$, $R_3 = CH_3$, $R_4 = OC_2H_5$, $n = 1$]

[S-(2-carbethoxypropyl)glutathione]

In 100 ml of water is dissolved 6.2 g of glutathione and the solution is adjusted to pH 7 with 2N-sodium hydroxide. To this solution is added 4 ml of ethyl methacrylate and the mixture is stirred at room temperature for 48 hours. Thereafter, 4.4 g of copper acetate is added and dissolved and the precipitated copper salt is collected by filtration and rinsed with water. This copper salt is suspended in 150 ml of water and hydrogen sulfide is bubbled through the suspension with stirring to precipitate the copper sulfide. This copper sulfide is filtered off and the filtrate is concentrated. The resulting white crystals are recovered by filtration and recrystallized from water to give 4.5 g of needlets melting at 193°–194° C. (decompn.) TLC, silica gel Rf=0.28 (n-butanol-acetic acid-water=4:1:1)

Elemental analysis, for $C_{16}H_{27}O_8N_3S$: Calcd. (%): C, 45.60; H, 6.46; N, 9.97. Found (%): C, 45.33; H, 6.65; N, 9.97.

SYNTHESIS EXAMPLE 3

S-[(2-Methyl-2-carbethoxyhydroxy)ethyl]glutathione

[$R_1 = R_2 = H$, $R_3 = CH_3$, $R_4 = OC_2H_4OH$, $n = 1$)

Using 6.2 g of glutathione and 3.3 g of 2-hydroxyethyl methacrylate, the procedure of Synthesis Example 2 is followed and the resulting crop of crystals is recrystallized from water-ethanol to give 4.5 g of white powdery crystals melting at 173°–175° C. (decompn.). TLC, silica gel Rf=0.19 (n-butanol-acetic acid-water=4:1:1).

Elemental analysis, for $C_{16}H_{27}O_9N_3S$: Calcd. (%): C, 43.93; H, 6.22; N, 9.60. Found (%): C, 43.64; H, 6.09; N, 9.72.

SYNTHESIS EXAMPLE 4

S-(2-Methyl-2-carbamoylethyl)glutathione

[$R_1 = R_2 = H$, $R_3 = CH_3$, $R_4 = NH_2$, $n = 1$]

Using 6.2 g of glutathione and 4.0 g of methacrylamide, the procedure of Synthesis Example 2 is followed and the resulting crop of crystals is recrystallized from water-ethanol to give 5.6 g of white crystals melting at 165°–167° C. (decompn.). TLC, silica gel Rf=0.14 (n-butanol-acetic acid-water=4:1:1)

Elemental analysis, for $C_{14}H_{24}O_7N_4S1/2H_2O$: Calcd. (%): C, 41.89; H, 6.28; N, 13.96. Found (%): C, 41.65; H, 6.11; N, 13.84.

SYNTHESIS EXAMPLE 5

S-(2-Carbethoxyethyl)glutathione

[$R_1 = R_2 = R_3H$, $R_4 = OC_2H_5$, $n = 1$]

Using 6.2 g of glutathione and 5 ml of ethylacrylate, the procedure of Synthesis Example 2 is followed and the resulting crop of crystals is recrystallized from water to give 6.0 g of white crystals melting at 194°–195° C. (decompn.). TLC, silica gel Rf=0.24 (n-butanol-acetic acid-water=4:1:1).

$[\alpha]_D^{20} -22.8°$ (c=1, $H_2O$).

Elemental analysis, for $C_{15}H_{25}O_8N_3S$: Calcd. (%): C, 44.22; H, 6.18; N, 10.31. Found (%): C, 44.08; H, 6.36; N, 10.46.

SYNTHESIS EXAMPLE 6

S-[2-Methyl-2-carbobenzoxyethyl]glutathione

[$R_1 = R_2 = H$, $R_3 = CH_3$, $R_4 = OCH_2C_6H_5$, $n = 1$]

A mixture of 6.2 g of glutathione and 3.8 g of benzyl methacrylate is stirred in a hydrous solvent (80 ml water, 80 ml ethanol) at room temperature for 48 hours and the reaction mixture is concentrated to about 40 ml. The residue is acidified with acetic acid and the resulting white crystalline precipitate is recovered by filtration. The crystals are dissolved in 2% sodium hydrogen carbonate, acidified with acetic acid and the resulting crop of white crystals is collected by filtration, washed with water and ethanol and dried.

Yield 4.5 g; m.p. 191°–192° C. (decompn.). TLC, silica gel Rf=0.34 (n-butanol-acetic acid-water=4:1:1).

SYNTHESIS EXAMPLE 7

S-(2-Methyl-2-carboisobutoxyethyl)glutathione

[$R_1=R_2=H$, $R_3=CH_3$, $R_4=OC_4H_9$, $n=1$]

Using 6.2 g of glutathione, 3.0 g of isobutyl methacrylate and, as a solvent, 100 ml water-50 ml ethanol, the procedure of Synthesis Example 2 is followed and the resulting crop of crystals is recrystallized from water to give 4.0 g of white crystals melting at 195°-196° C. (decompn.) TLC, silica gel Rf=0.34 (n-butanol-acetic acid-water=4:1:1).

Elemental analysis, for $C_{18}H_{31}O_8N_3S$: Calcd. (%): C, 48.10; H, 6.95; N, 9.35. Found (%): C, 47.96; H, 6.82; N, 9.37.

SYNTHESIS EXAMPLE 8

S-(2-Methyl-2-carbethoxyethyl)glutathione isopropyl ester

[$R_1=C_3H_7$, $R_2=H$, $R_3=CH_3$, $R_4=OC_2H_5$, $n=1$]

In 50 ml of water is suspended 4.0 g of glutathione isopropyl ester sulfate and the solution is adjusted to pH 6.5 with 2N-sodium hydroxide. After 2 ml of ethyl methacrylate is added, the mixture is stirred at room temperature for 3 hours and concentrated. To the residue is added ethanol and the precipitated inorganic salt is filtered off. To the filtrate is added acetone and the resulting crop of colloidal crystals is recovered by filtration and purified by Sephadex G-10 column chromatography (eluent: water-ethanol=1:1). Recrystallization from ethanol-acetone gives 2.4 g of amorphous crystals. TLC, silica gel Rf=0.48 (n-butanol-acetic acid-water=4:1:1)

Elemental analysis, for $C_{19}H_{33}O_8N_3S$: Calcd. (%) C, 49.23; H, 7:18; N, 9.06. Found (%): 49.09; H, 7.10; N, 9.16.

SYNTHESIS EXAMPLE 9

S-(2-Methyl-2-carbiosobutoxyethyl)glutathione isopropyl ester

[$R_1=C_3H_7$, $R_2=H$, $R_3=CH_3$, $R_4=OC_4H_9$, $n=1$]

Using 4.0 g of glutathione isopropyl ester sulfate and 1.6 g of isobutyl methacrylate, the procedure of Synthesis Example 8 is followed (stirring time: 48 hours). The resulting crop of crystals is recrystallized from ethanol-ethyl acetate-petroleum benzin to give 2.0 g of colorless amorphous crystals. TLC, silica gel Rf=0.54 (n-butanol- acetic acid-water=4:1:1)

Elemental analysis, for $C_{21}H_{37}O_8N_3S$: Calcd. (%): C, 51.31; H, 7.59; N, 8.55. Found (%): C, 51.13; H, 7.48; N, 8.57.

SYNTHESIS EXAMPLE 10

S-(1-Methyl-2-carboisopropoxyethyl)glutathione

[$R_1=R_3=H$, $R_2=CH_3$, $R_4=OC_3H_7$, $n=1$]

Using 6.2 g of glutathione and 3.7 g of isopropyl crotonate, the procedure of Synthesis Example 7 is followed and the resulting crop of crystals is recrystallized form water to give 3.2 of white crystals melting at 189°-190° C. (decompn.). TLC., silica gel Rf=0.27 (n-butanol-acetic acid-water=4:1:1).

Elemental analysis, for $C_{17}H_{29}O_8N_3S$: Calcd. (%): C, 46.89; H, 6.71; N, 9.65. Found (%): C, 46.66; H, 6.53; N, 9.68.

SYNTHESIS EXAMPLE 11

S-(1-Phenyl-2-carbethoxyethyl)glutathione

[$R_1=R_3=H$, $R_2=C_6H_5$, $R_4=OC_2H_5$, $n=1$]

Using 6.2 g of glutathione and 4.0 g of ethyl cinnamate, the procedure of Synthesis Example 7 is followed (stirring at room temperature for about 7 days) and the resulting crop of crystals is recrystallized from water to give 2.7 g of white needles melting at 185°-186° C. (decompn.). TLC, silica gel Rf=0.29 (n-butanol-acetic acid-water=4:1:1).

Elemental analysis, for $C_{21}H_{29}O_8N_3S \cdot 1/2H_2O$: Calcd. (%): C, 51.21; H, 6.14; N, 8.53. Found (%): C, 51.14; H, 5.89; N, 8.42.

SYNTHESIS EXAMPLE 12

S-(Carboisopropoxymethyl)glutathione

[$R_1=R_3=H$, $R_4=OC_3H_7$, $n=0$]

In 80 ml of water is dissolved 6.2 g of glutathione and the solution is adjusted to pH 6.5 with 2 N-sodium hydroxide. Following addition of 5 g of isopropyl monochloroacetate, the mixture is stirred at room temperature. The pH of the mixture fell with progress of the reaction. Therefore, the reaction mixture is readjusted to pH 6.5 with 2 N-sodium hydroxide. This procedure is repeated and when the pH has almost ceased to fall, 2 ml of acetic acid and a sufficient amount of water are added to make a total of 200 ml. Then, 4.4 g of copper acetate is added and dissolved and the precipitated copper salt is recovered by filtration, washed with water and methanol and suspended in 200 ml of water. Then, hydrogen sulfide is bubbled through the suspension with stirring and the resulting copper sulfide is filtered off, the filtrate is concentrated and the resulting crop of white crystals is harvested by filtration and recrystallized from water to give 5.2 g of white crystals melting at 194°-195° C. (decompn.). TLC, silica gel Rf=0.21 (n-butanol-acetic acid-water=4:1:1).

$[\alpha]_D^{20} -29.0°$ (c=1.0, $H_2O$).

Elemental analysis, for $C_{15}H_{25}O_8N_3S$: Calcd. (%): C, 44.22; H, 6.18; N, 10.31. Found (%): C, 44.10; H, 6.24; N, 10.26.

TEST EXAMPLE 1

Effect on acetaminophen-induced hepatic impairment

Method; Male SD rats (body weights ca. 180 g) purchased form Japan SLC were used. The test substance was orally administered (0.5 mmole/kg) and one hour later 300 mg/kg of acetaminophen was intraperitoneally administered. After 24 hours, blood was drawn from the abdominal aorta and the serum was separated. Using this serum, s-GOT and GPT were determined.

Result: Nine different glutathione derivatives were tested for inhibitory effect on acetaminophen-induced hepatic impairment. As shown in Table 1, compound Nos. 1, 2, 3, 4, 7, 8 and 9 (corresponding to the structures indicated int he table) showed significant antihepatopathic effects.

TABLE 1

Effect on acetaminophen-induced hepatic impairment

| No. | Test substance | s-GOT | | s-GPT | |
|---|---|---|---|---|---|
| — | Physiological saline (control) | 5269 ± 835 | | 2060 ± 494 | |
| 1 | $R_1 = R_2 = H, R_3 = CH_3, R_4 = OH, n = 1$ | 1259 ± 424*[3] | (76.1) | 337 ± 117*[1] | (83.6) |
| 2 | $R_1 = R_2 = H, R_3 = CH_3, R_4 = OC_2H_5, n = 1$ | 841 ± 354*[2] | (84.0) | 195 ± 81*[2] | (90.5) |
| 3 | $R_1 = R_2 = R_3 = H, R_4 = OH, n = 1$ | 1968 ± 626*[2] | (62.6) | 530 ± 180*[1] | (74.3) |
| 4 | $R_1 = R_2 = R_3 = H, R_4 = OC_2H_5, n = 1$ | 1935 ± 530*[2] | (63.3) | 598 ± 226*[1] | (71.0) |
| 5 | $R_1 = R_2 = H, R_3 = CH_3, R_4 = OC_4H_9, n = 1$ | 2972 ± 803 | (43.6) | 1384 ± 417 | (32.8) |
| 6 | $R_1 = R_2 = H, R_3 = CH_3, R_4 = OCH_2C_6H_5, n = 1$ | 2968 ± 824 | (43.7) | 1384 ± 421 | (32.8) |
| 7 | $R_1 = C_3H_7, R_2 = H, R_3 = CH_3, R_4 = OC_2H_5, n = 1$ | 1570 ± 511*[2] | (70.2) | 529 ± 168*[1] | (74.3) |
| 8 | $R_1 = C_3H_7, R_2 = H, R_3 = CH_3, R_4 = OC_4H_9, n = 1$ | 163 ± 89*[3] | (96.9) | 52 ± 29*[2] | (97.5) |
| 9 | $R_1 = R_3 = H, R_2 = CH_3, R_4 = OC_3H_7, n = 1$ | 171 ± 71*[3] | (96.8) | 43 ± 21*[2] | (97.9) |

Unit: IU/l; each value represents the mean ± S.E.;
n = 7–10; the figure in parentheses represents % inhibition.
Significant difference from physiological saline:
*[1]. $p < 0.05$;
*[2]. $p < 0.01$;
*[3]. $p < 0.001$.

BEST MODES OF WORKING THE INVENTION

PREPARATION EXAMPLE 1

Oral tables

| S-(2-Methyl-2-carboisobutoxyethyl)glutathione isopropyl ester | 100 mg |
|---|---|
| Lactose | 80 mg |
| Starch | 17 mg |
| Magnesium stearate | 3 mg |

Using the above materials per tablet, tablets for oral administration were manufactured by the established pharmaceutical procedure. Where necessary, the tablets may be sugar-coated.

PREPARATION EXAMPLE 2

Injection

| S-(1-Methyl-2-carboisopropoxyethyl)glutathione | 1.0 g |
|---|---|
| Sodium chloride | 0.6 g |
| Distilled water for injection | 100 ml |

The above materials are admixed, adjusted to pH 6.5 with 2N-sodium hydroxide and sterilized by filtration. The filtrate is aseptically distributed in 2 ml portions into glass ampules and sealed by fusion of the glass to provide a batch of injections.

We claim:

1. An antihepatopathic composition comprising an antihepatopathy effective amount of a compound of the formula

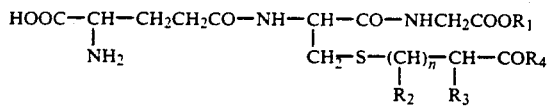

wherein $R_1$ and $R_3$ are the same or different and are respectively a hydrogen atom or a lower alkyl group; $R_4$ is a hydroxyl group, a lower alkoxy group which is unsubstituted or is substituted by a hydroxyl group or a phenyl group or an amino group; n means 0 or 1 and when n = 1, $R_2$ is a hydrogen atom, a lower alkyl group or a phenyl group or a pharmaceutically acceptable salt thereof as an active ingredient, and a pharmaceutically acceptable carrier.

2. An antihepatopathic composition according to claim 1 wherein the compound is S-(2-carboxyethyl)-glutathione.

3. An antihepatopathic composition according to claim 1 wherein the compound is S-(2-methyl-2-carbethoxyethyl)glutathione.

4. An antihepatopathic composition according to claim 1 wherein the compound is S-[(2-methyl-2-carbethoxyhydroxy)ethyl]glutathione.

5. An antihepatopathic composition according to claim 1 wherein the compound is S-(2-methyl-2-carbamoylethyl)glutathione.

6. An antihepatopathic composition according to claim 1 wherein the compound is S-(2-carbethoxyethyl)glutathione.

7. An antihepatopathic composition according to claim 1 wherein the compound is S-(2-methyl-2-carbobenzoxyethyl)glutathione.

8. An antihepatopathic composition according to claim 1 wherein the compound is S-(2-methyl-2-carboisobutoxyethyl)glutathione.

9. An antihepatopathic composition according to claim 1 wherein the compound is S-(2-methyl-2-carbethoxyethyl)glutathione isopropyl ester.

10. An antihepatopathic composition according to claim 1 wherein the compound is S-(2-methyl-2-carboisobutoxyethyl)glutathione isopropyl ester.

11. An antihepatopathic composition according to claim 1 wherein the compound is S-(1-methyl-2-carboisopropoxyethyl)glutathione.

12. An antihepatopathic composition according to claim 1 wherein the compound is S-(1-phenyl-2-carboethoxyethyl)glutathione.

13. An antihepatopathic composition according to claim 1 wherein the compound is S-(carboisopropoxymethyl)glutathione.

* * * * *